(12) United States Patent
Hwang et al.

(10) Patent No.: US 8,664,377 B2
(45) Date of Patent: Mar. 4, 2014

(54) METHOD AND APPARATUS FOR ISOLATING NUCLEIC ACIDS

(75) Inventors: Kyu-youn Hwang, Yongin-si (KR); Joon-ho Kim, Seongnam-si (KR); Kak Namkoong, Seoul (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 306 days.

(21) Appl. No.: 12/852,824

(22) Filed: Aug. 9, 2010

(65) Prior Publication Data

US 2011/0077388 A1 Mar. 31, 2011

(30) Foreign Application Priority Data

Sep. 30, 2009 (KR) ......................... 10-2009-0093214
Dec. 22, 2009 (KR) ......................... 10-2009-0129134

(51) Int. Cl.
*C07H 21/00* (2006.01)
(52) U.S. Cl.
USPC ...................................... 536/25.41
(58) Field of Classification Search
None
See application file for complete search history.

(56) References Cited

U.S. PATENT DOCUMENTS

| 5,374,522 A | | 12/1994 | Murphy et al. |
| 5,491,133 A | * | 2/1996 | Walder et al. ............... 514/44 R |
| 5,997,742 A | * | 12/1999 | Gjerde et al. ................ 210/635 |
| 6,111,096 A | * | 8/2000 | Laugharn et al. ............ 204/601 |
| 6,274,726 B1 | * | 8/2001 | Laugharn et al. ............ 536/25.4 |
| 6,440,725 B1 | | 8/2002 | Pourahmadi et al. |
| 2002/0016450 A1 | | 2/2002 | Laugharn et al. |
| 2007/0148649 A1 | | 6/2007 | Shigesada et al. |
| 2008/0051572 A1 | | 2/2008 | Chung et al. |

FOREIGN PATENT DOCUMENTS

| EP | 2017339 A1 | 1/2009 |
| JP | 2005278438 | 10/2005 |
| JP | 2006006258 | 1/2006 |
| JP | 2008220380 | 9/2008 |
| KR | 1020060039710 A | 5/2006 |
| KR | 1020060058528 A | 5/2006 |
| KR | 20080027134 A | 3/2008 |

* cited by examiner

*Primary Examiner* — Layla Bland
(74) *Attorney, Agent, or Firm* — Leydig, Voit & Mayer, Ltd.

(57) ABSTRACT

A method and apparatus for efficiently isolating nucleic acids from a nucleic acid-containing sample.

6 Claims, 4 Drawing Sheets

METHOD AND APPARATUS FOR ISOLATING NUCLEIC ACIDS

CROSS-REFERENCE TO RELATED APPLICATIONS

This application claims priority to Korean Patent Application No. 10-2009-0093214, filed on Sep. 30, 2009 and Korean Patent Application No. 10-2009-0129134, filed on Dec. 22, 2009, and all the benefits accruing therefrom under 35 U.S.C.§119, the contents of which in their entirety is herein incorporated by reference.

BACKGROUND

1. Field

The present disclosure relates to methods and apparatuses for efficiently isolating nucleic acids.

2. Description of the Related Art

Methods of isolating nucleic acids are known in the art. For example, commercially available apparatuses for isolating nucleic acids include apparatuses using magnetic beads and apparatuses using filter columns. The apparatuses isolate nucleic acids in amounts ranging from several to tens of micrograms (μg), and the concentration of nucleic acids to be extracted is in the range of several to tens of nanograms per microliter (ng/μl). Molecular diagnostic methods, which utilize nucleic acids, require a high concentration of nucleic acids, i.e., hundreds of ng/μl or greater, however, it is difficult to obtain an eluent containing a sufficiently high concentration of nucleic acid from such apparatuses.

In order to obtain a high concentration of nucleic acids, the volume of eluent ranges from several to tens of microliters (μl). However, in apparatuses for isolating nucleic acids that utilize magnetic beads, when the magnetic beads are collected using a magnetic field in a nucleic acid isolation process, the magnetic beads are collected along with the eluent in which the magnetic beads are dispersed. Thus, it is difficult to collect the eluent, resulting in poor elution efficiency. In apparatuses for isolating nucleic acids that utilize filter columns, nucleic acids are bound to the entire surface area of a filter in a column. As a result, during the elution process, it is difficult to elute all of the bound nucleic acids using only a small amount of an eluent. Accordingly, it is difficult to elute a high concentration of nucleic acids.

Therefore, there is still a need for a method and apparatus for more efficiently isolating nucleic acids.

SUMMARY

Disclosed herein are methods of isolating nucleic acids, the methods including dispersing a solid support in an eluent by adjusting the pressure of a gas or the intensity of an ultrasonic wave. Also disclosed herein are apparatuses for isolating nucleic acids.

In one embodiment, the method includes contacting a nucleic acid-containing sample with a nucleic acid-binding solid support to bind a nucleic acid to the nucleic acid-binding solid support, thereby forming a nucleic acid-solid support complex; adding an eluent to the nucleic acid-solid support complex; dispersing the nucleic acid-solid support complex in the added eluent; and separating the eluent from the nucleic acid-binding solid support.

In one embodiment, the apparatus includes a filter column having disposed therein a nucleic acid-binding solid support or a nucleic acid-solid support complex, wherein the filter column includes a top opening, a bottom opening, and a filter disposed therein; and a dispersion unit connected to the filter column to disperse the nucleic acid-binding solid support or the nucleic acid-solid support complex in a liquid.

BRIEF DESCRIPTION OF THE DRAWINGS

The above and other aspects, advantages and features of this disclosure will become more apparent by describing in further detail exemplary embodiments thereof with reference to the accompanying drawings in which.

DETAILED DESCRIPTION

Figure 1:
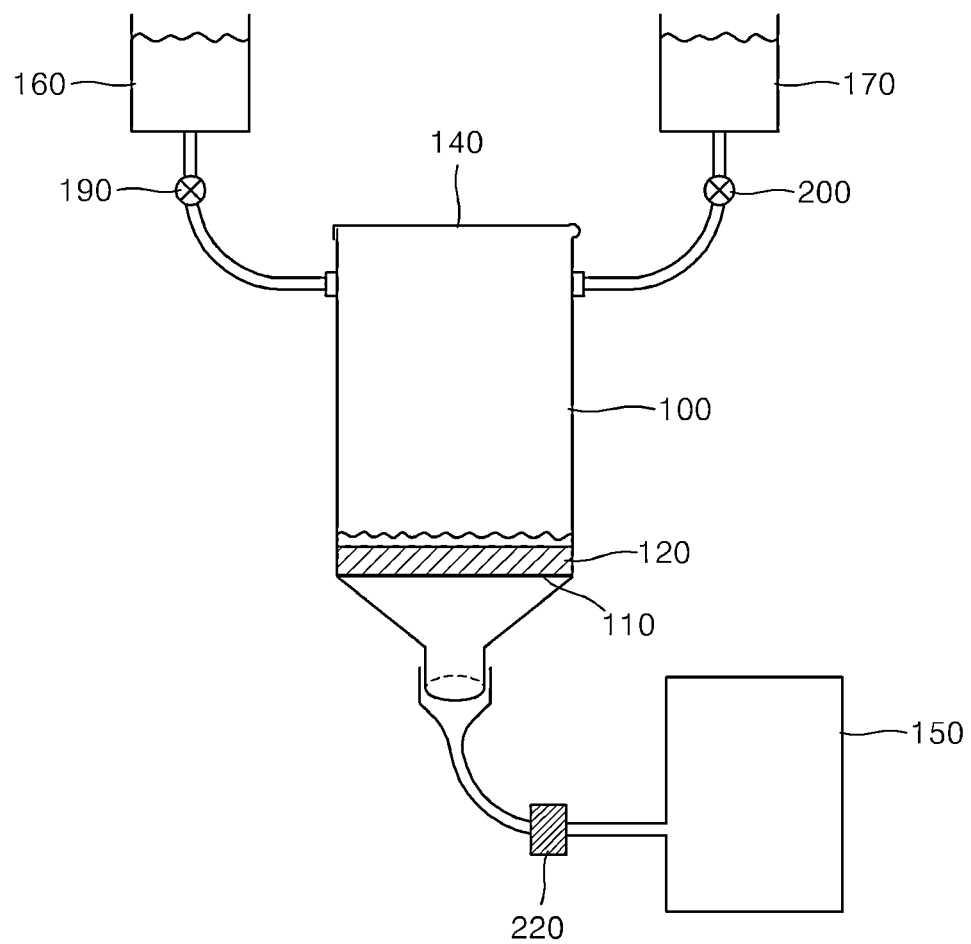
FIG. 1 is a view of an exemplary embodiment of an apparatus for isolating nucleic acids, which includes a pressurizing device as a dispersion unit.

The invention now will be described more fully hereinafter with reference to the accompanying drawings, in which various embodiments are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings herein.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The term "lower," can therefore, encompass both an orientation of "lower" and "upper," depending on the particular orientation of the figure. Similarly, if the device in one of the figures is turned over, elements described as "below" or "beneath" other elements would then be oriented "above" the other elements. The terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

Reference will now be made in detail to embodiments, examples of which are illustrated in the accompanying drawings. In an embodiment, a method of isolating nucleic acids includes contacting a nucleic acid-containing sample with a nucleic acid-binding solid support to bind a nucleic acid to the nucleic acid-binding solid support, thereby forming a nucleic acid-solid support complex; adding an eluent to the nucleic acid-solid support complex; dispersing the nucleic acid-solid support complex in the added eluent; and separating the eluent from the nucleic acid-binding solid support.

The binding efficiency of the nucleic acid-binding solid support to the nucleic acid is 70% or greater. In addition, the dispersing is performed by adjusting the pressure of a gas or the intensity of an ultrasonic wave for a constant period of time.

The method will now be described in more detail.

The method may include contacting a nucleic acid-containing sample with a nucleic acid-binding solid support to bind a nucleic acid to the nucleic acid-binding solid support, thereby forming a nucleic acid-solid support complex.

The term "nucleic acid" used herein is understood as a collective term, encompassing DNA (for example, gDNA and cDNA) and RNA molecules containing nucleotides. Nucleotides, which are the basic structural units of nucleic acids, are understood to include natural nucleotides, and nucleotide analogues in which sugars or bases are modified.

The contacting of the nucleic acid-containing sample with a nucleic acid-binding solid support may be performed by adding the nucleic acid-containing sample to the nucleic acid-binding solid support and directly mixing them together.

The nucleic acid-containing sample used in the contacting may be any sample that contains nucleic acids. The nucleic acid-containing sample may be a biological sample or non-biological sample. The biological sample includes, for example, viruses, bacteria, tissues, cells, or components thereof, and the like. The non-biological sample includes, for example, synthesized nucleic acid products and PCR amplification products, but is not limited thereto. In addition, to facilitate the binding of nucleic acids contained in the biological sample with the nucleic acid-binding solid support, an extract that is removed from the biological sample using various methods known in the art, may also be used in the contacting operation.

The binding efficiency of the nucleic acid-binding solid support to the nucleic acids may be about 70% or greater, or specifically about 90% or greater. The binding efficiency represents a degree of binding between the nucleic acid-binding solid support and the nucleic acids, and may be a binding affinity or binding amount. For example, a binding efficiency of 70% indicates that the amount of the nucleic acid-binding solid support used is 70 wt % based on 100 wt % of the total nucleic acids contained in the nucleic acid-containing sample.

When the nucleic acid-containing sample is a non-biological sample, the amount of the nucleic acid-binding solid support to be used may be determined by measuring the total amount of nucleic acids contained in the nucleic acid-containing sample. When the nucleic acid-containing sample is a biological sample, the amount of the nucleic acid-binding solid support may be determined by measuring the amount of nucleic acids contained in an extract of the biological sample. The amount of the nucleic acid-binding solid support used is greater than the total amount of nucleic acids contained in the nucleic acid-containing sample used, and thus all of the nucleic acids are able to sufficiently bind to the nucleic acid-binding solid support, thereby resulting in an increase in the elution efficiency of the nucleic acids. The nucleic acid-binding solid support with the nucleic acids bound thereto (e.g., nucleic acid-solid support complex), may be packed on a filter within a filter column of an apparatus for isolating nucleic acids. The pore size of the filter may be smaller than the size of the nucleic acid-binding solid support with the nucleic acids bound thereto in order to be packed on the filter. In one embodiment, the nucleic acid-binding solid support with the nucleic acids bound thereto may have a diameter of about 0.1 μm to about 50 μm.

The nucleic acid-binding solid support used in the contacting may be selected from the group consisting of a slide, a wafer, a bead, a membrane, and a plate. In an embodiment, the nucleic acid-binding solid support is a bead. The bead may be selected from the group consisting of a magnetic bead, a silica bead, a polystyrene bead, a glass bead, and a cellulose bead, but is not limited thereto. In another embodiment, the nucleic acid-binding solid support has a diameter from about 0.1 μm to about 50 μm. The nucleic acid-binding solid support has nucleic acid-binding properties. That is, the nucleic acid-binding solid support may bind nucleic acids via a non-covalent bond, such as an ionic bond, adsorption, or the like. For example, the surface of the nucleic acid-binding solid support may itself have a functional group that binds the nucleic acids, or alternatively, the surface of the nucleic acid-binding solid support may be coated with the functional group. The functional group that binds the nucleic acids may be, for example, an amine-based functional group or a carboxyl-based functional group, but is not limited thereto.

The method may further include washing the nucleic acid-binding solid support to remove any remaining, unbound nucleic acid-containing sample after the contacting. The washing may be performed using washing solutions known in the art. The washing solution may be any solution that does not affect the binding of the nucleic acids that are bound to the nucleic acid-binding solid support, and which removes materials, such as unbound nucleic acids and the like, that are not bound to the nucleic acid-binding solid support. For example, the washing solution may be a solution that does not affect the binding of nucleic acids that are bound to the nucleic acid-binding solid support, and which removes any impurities that may adversely affect subsequent processes. In an embodiment, after the contacting, washing may be performed by adding 70% ethanol to the nucleic acid-binding solid support and then removing nucleic acids not bound to the nucleic acid-binding solid support by centrifugation or drying. The impurities contained in the nucleic acid-containing sample are removed by the washing. Therefore, impurities that may exist in the nucleic acid-solid support complex are removed, and as a result, the nucleic acids are eluted more efficiently and the purity of the nucleic acids is increased.

In an embodiment, the method includes adding an eluent to the nucleic acid-solid support complex and dispersing the nucleic acid-solid support complex in the eluent.

The dispersing may be performed by adjusting the pressure of a gas or by adjusting the intensity of an ultrasonic wave for a constant period of time.

The eluent is added to isolate or separate the nucleic acid of the nucleic acid-solid support complex formed in the contacting from the nucleic acid-binding solid support. The term "nucleic acid-solid support complex" used herein refers to a complex in which a nucleic acid is bound to the nucleic acid-binding solid support via a non-covalent bond, such as a hydrogen bond, van der Waals force, an ionic bond, or hydrophobic interaction.

The eluent may have a pH of about 5 to about 12. An eluent having a pH within this range may be used to disperse the nucleic acid-solid support complex therein. Examples of eluents include water, Tris-HCl, and the like. In addition, in order to isolate nucleic acids in a high concentration, the amount of the eluent used may be about 5 $\mu$l to about 1000 $\mu$l, specifically about 5 $\mu$l to about 500 $\mu$l, or more specifically about 5 $\mu$l to about 100 $\mu$l.

The dispersing may be performed together with the addition of a pressurized gas or ultrasonic waves. The nucleic acid-solid support complex may be dispersed in the eluent by the addition of the pressurized gas or the addition of ultrasonic waves. In addition, the dispersing may be performed by adjusting or repeatedly adjusting (that is, adjusting at least twice) the pressure of a gas (that is, pressurizing and depressurizing). Alternatively, the nucleic acid-solid support complex may be dispersed in the eluent by adjusting or repeatedly adjusting the intensity of an ultrasonic wave (that is, addition and non-addition) for a constant period of time. The nucleic acid-solid support complex may be dispersed in the eluent by pressurizing and depressurizing a gas, or by the addition and non-addition of ultrasonic waves. In particular, the gas or ultrasonic wave is pressurized and depressurized, or added and non-added, by performing a cycle that includes a pulse of about 1 to about 10 seconds sequentially followed by a rest period of about 1 to about 20 seconds. For example, the cycle may be performed 1 to about 200 times, specifically 2 to about 200 times, specifically about 5 to about 100 times, or more specifically about 10 to about 50 times. The pressuring and depressurizing (pressurized gas), or addition or non-addition (ultrasonic waves), may be automatically performed through the use of a program. When the pressurized gas is added, the pressurized gas has a pressure of about 0.01 Pa to about 200 kPa, specifically about 0.1 Pa to about 100 kPa, or more specifically about 1 Pa to about 100 kPa, with respect to atmospheric pressure. When ultrasonic waves are used, the ultrasonic waves added have a frequency of about 15 kHz to about 400 kHz, specifically about 30 kHz to about 200 kHz, or more specifically about 50 kHz to about 100 kHz.

In one embodiment, the method includes separating the eluent from the nucleic acid-binding solid support.

In the separating step, the eluent into which nucleic acids are eluted from the nucleic acid-solid support complex is separated from the nucleic acid-binding solid support, thereby obtaining only the eluent containing the eluted nucleic acids. As described above, the nucleic acid that is bound to the nucleic acid-binding solid support is chemically isolated from the nucleic acid-binding solid support using the eluent, and is even more efficiently isolated by the use of external physical force generated by pressurizing and depressurizing a pressurized gas, or by the addition and non-addition of ultrasonic waves. The eluent containing the isolated nucleic acid may be separated from the nucleic acid-binding solid support using separation methods known in the art. Examples of known separation methods include centrifugation, a pressurized gas, vacuum, or the like.

In an embodiment, an apparatus for isolating nucleic acids includes a filter column having disposed therein a nucleic acid-binding solid support or a nucleic acid-solid support complex, wherein the filter column includes a top opening, a bottom opening, and a filter disposed therein; and a dispersion unit that is connected to the filter column to disperse the nucleic acid-binding solid support or the nucleic acid-solid support complex in a liquid.

In another embodiment, the apparatus may further include a dispersion adjustment unit for adjusting an operation of the dispersion unit.

A detailed description of the nucleic acid-binding solid support is provided below. The filter column that is filled with the nucleic acid-binding solid support may be prepared using a methods known in the art, for example, by directly filling a commercially available empty filter column with the nucleic acid-binding solid support, or a commercially available filter column that is already filled with the nucleic acid-binding solid support. In addition, the nucleic acid-binding solid support contained in the filter column may be bound to nucleic acids prior to filling of the filter column. That is, the nucleic acid-binding solid support may be contained in the filter column in the form of a nucleic acid-solid support complex.

The filter column may be, for example, a spin column manufactured by Qiagen. In an embodiment, the filter column is formed of an ultrasonically transparent material (that is, a material that allows the transmission of ultrasound), and may be selected from the group consisting of metal, ceramic, glass, and plastic, but is not limited thereto. The filter column may be in the form of a cone with a cylinder-shaped body and a bottom opening. The lower portion of the filter column is filled with the nucleic acid-binding solid support or the nucleic acid-solid support complex. The bottom opening of the filter column may include a filter that includes pores having a smaller size than particles of the nucleic acid-binding solid support, or particles of the nucleic acid-solid support complex, in order to prevent the nucleic acid-binding solid support or the nucleic acid-solid support complex from escaping from the filter column.

The dispersion unit may be a unit that disperses the nucleic acid-binding solid support or the nucleic acid-solid support complex in a liquid. The dispersion unit may be, for example, a pressurizing device that pressurizes the nucleic acid-binding solid support or the nucleic acid-solid support complex. Alternatively, the dispersion unit may be a sonicator that provides the nucleic acid-binding solid support or the nucleic acid-solid support complex with ultrasonic waves. The pressurizing device or the sonicator may be connected to the top opening or the bottom opening of the filter column. In an embodiment, the pressurizing device or the sonicator is connected to a bottom opening of the filter column, disposed to correspond to the elution direction of the nucleic acid eluent, or to a top opening of the filter column, disposed to correspond to the direction opposite the elution direction of the nucleic acid eluent, so as to allow fluid flow therebetween. In another embodiment, the pressurizing device or the sonicator may be detachably installed. For example, the pressurizing device may be connected to the bottom opening of the filter column via a tube made of rubber.

Meanwhile, to prevent materials in the filter column from leaking to the outside, the filter column may further include a cover for opening or closing the top opening of the filter column. In this regard, the cover is disposed at the side opposite to the pressurizing device or the sonicator. Therefore, a nucleic acid-containing sample, a nucleic acid-solid support complex, a washing solution, or an eluent may be manually added to the filter column when the cover is opened. The cover may further include an air vent hole for ventilating air.

If a pressurizing device is used as the dispersion unit in the apparatus, the pressurizing device may be connected to the bottom opening of the filter column such that the pressurized device is disposed to correspond to the elution direction of the nucleic acid eluent, to allow fluid flow therebetween. The pressurizing device may be a device for adjusting pressure via a dispersion adjustment unit. The adjustment of the pressure may be automatically performed using a program. By adjusting the pressurizing device, a pressurized gas (e.g. nitrogen gas) is injected to the eluent containing the nucleic acid-solid support complex existing on the filter column, and a gas pressurized within the ranges of pressure and time described above is pressurized and depressurized to disperse the nucleic acid-solid support complex in the eluent. Alternatively, if a sonicator is used as the dispersion unit in the apparatus, ultrasonic waves are added or non-added to disperse the nucleic acid-solid support complex in the eluent.

If a sonicator is used as the dispersion unit, an oscillator of the sonicator may be disposed inside the filter column. In one embodiment, the oscillator is disposed within the filter column such that the oscillator is within a group of the nucleic acid-binding solid support or a group of the nucleic acid-solid support complex. The sonicator may be a device for adjusting the addition and non-addition of ultrasonic waves via a dispersion adjustment unit. The addition and non-addition of ultrasonic waves may be automatically adjusted using a program. The oscillator oscillates the eluent that contains the nucleic acid-solid support complex by the addition and non-addition of ultrasonic waves in order to disperse the nucleic acid-solid support complex in the eluent.

The apparatus for isolating nucleic acids may further include a washing solution storage unit that provides the filter column with the washing solution and which is detachably installed. The apparatus may further include an eluent storage unit that provides the filter column with the eluent and which is detachably installed. The apparatus may further include a sample storage unit that provides the filter column with the sample and which is detachably installed.

The washing solution storage unit, the eluent storage unit, and the sample storage unit may be connected to an opening of the filter column which is disposed to correspond to the elution direction of nucleic acids, or an opening of the filter column which is disposed to correspond to a direction opposite to the elution direction of nucleic acids. The washing solution storage unit, the eluent storage unit, and the sample storage unit may be connected to the filter column via a passage that connects the washing solution storage unit, the eluent storage unit, and the sample storage unit with the opening of the filter column which is disposed to correspond to the elution direction of nucleic acids, or the opening of the filter column which is disposed to correspond to the direction opposite to the elution direction of nucleic acids. The washing solution storage unit, the eluent storage unit, and the sample storage unit may be connected to the filter column via a tube to allow fluid flow therebetween. The flow of the washing solution, the eluent, and the sample to the filter column are adjusted manually or automatically by a first adjustment unit, a second adjustment unit, and a third adjustment unit that are respectively connected to the washing solution storage unit, the eluent storage unit, and the sample storage unit. The apparatus may further include a waste liquid storage unit for storing a waste liquid generated from the filter column. that the waste liquid storage unit is connected to the bottom opening of the filter column which is disposed to correspond to the elution direction of nucleic acids, and to allow fluid flow therebetween.

One or more embodiments of the present invention will be described in further detail below with reference to the following examples. These examples are for illustrative purposes only and are not intended to limit the scope of the present invention.

Figure 2:
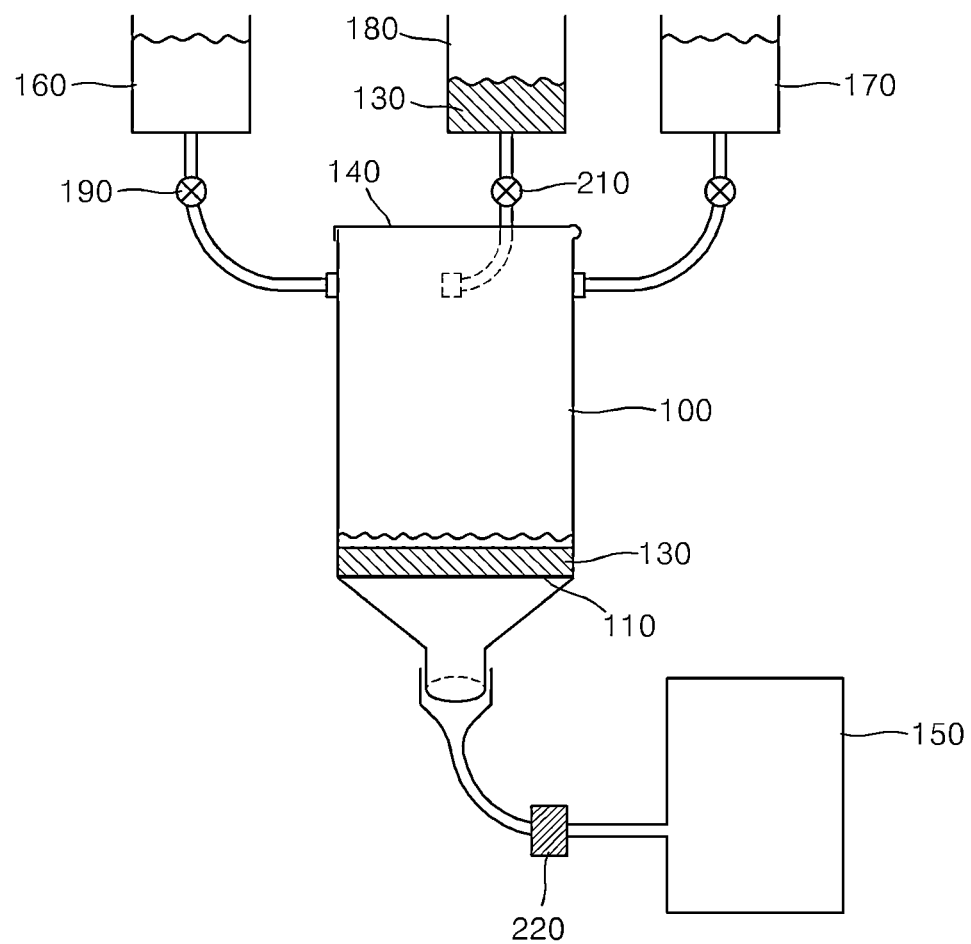
FIG. 2 is a view of an exemplary embodiment of an apparatus for isolating nucleic acids, which includes a pressurizing device as a dispersion unit and a sample storing unit.
Figure 3:
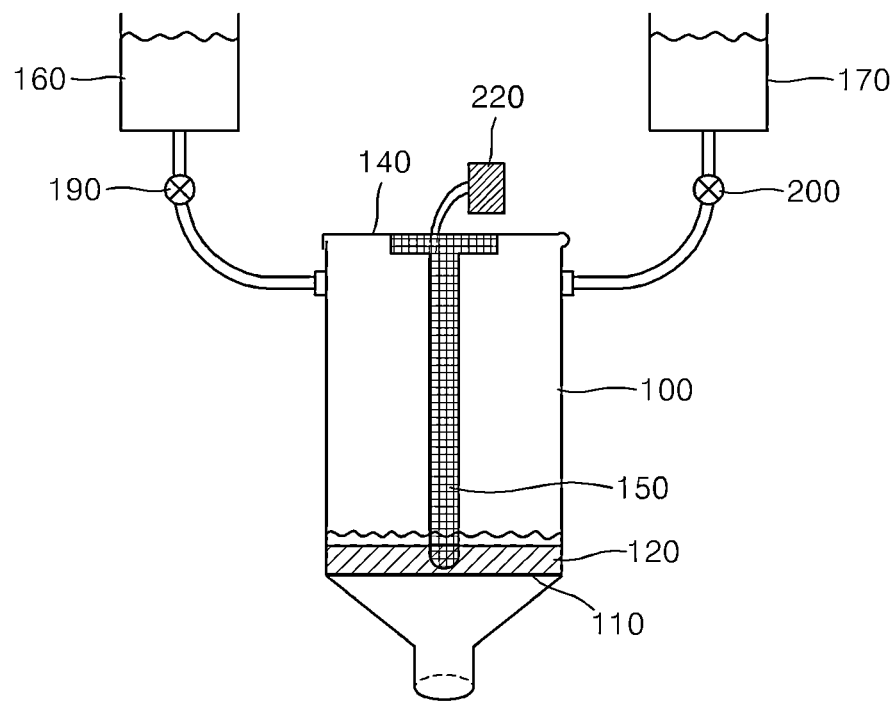
FIG. 3 is a view of an exemplary embodiment of an apparatus for isolating nucleic acids, which includes a sonicator as a dispersion unit.
Figure 4:
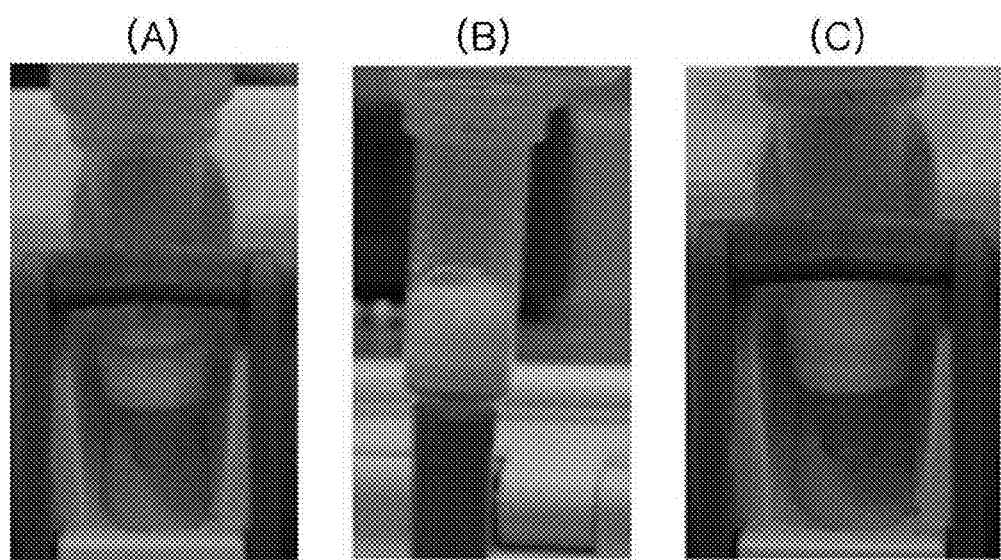
FIG. 4 is photographic images showing results for an exemplary embodiment of a method of isolating nucleic acids using an apparatus for isolating nucleic acids, and respectively shows images before (A), during (B) and after (C) dispersion of the beads.

FIGS. 1 through 3 are views of exemplary embodiments illustrating apparatuses for isolating nucleic acids.

In an embodiment, an apparatus for isolating nucleic acids is provided. Referring to FIGS. 1 through 3, the apparatus includes a filter column 100 that may be filled with a nucleic acid-binding solid support 120 or a nucleic acid-solid support complex 130, and which includes a filter 110; and a dispersion unit 150, that is disposed inside or outside the filter column 100, to disperse the nucleic acid-binding solid support 120 or the nucleic acid-solid support complex 130 in a liquid. The apparatus may further include a cover 140 for covering an opening of the filter column 100 to prevent materials in the filter column 100 from leaking to the outside in the dispersion process. The apparatus may further include a washing solution storage unit 160, an eluent storage unit 170, or a sample storage unit 180 that is connected to the apparatus to allow fluid flow therebetween. The apparatus may further include a dispersion adjustment unit 220 that adjusts the dispersion unit 150, and may further include a first adjustment unit 190, a second adjustment unit 200, and a third adjustment unit 210 that respectively adjust the amount of liquids stored in the washing solution storing unit 160, the eluent storing unit 170, and the sample storing unit 180.

A method of isolating nucleic acids will now be described with reference to FIGS. 1 through 3. A nucleic acid-containing sample is supplied to the filter column 100 that is filled with the nucleic acid-binding solid support 120 in order to contact the nucleic acid-binding solid support 120 with a nucleic acid, thereby forming a nucleic acid-solid support complex in which the nucleic acid binds with the nucleic acid-binding solid support 120. To remove the impurities present in the nucleic acid-containing sample, the nucleic acid-solid support complex is washed using a washing solution. The washing solution may be directly injected to the filter column 100 manually, or may be supplied from the washing solution storage unit 160. The washing solution storage unit is detachably connected to an opening of the filter column 100 which is disposed to correspond to the elution direction of nucleic acids, or an opening of the filter column 100 which is disposed to correspond to the direction opposite to the elution direction of nucleic acids. The flow of the washing solution from the washing solution storage unit 160 to the filter column 100 may be adjusted by the first adjustment unit 190 that is connected to the washing solution storage unit 160.

The eluent is then added to the filter column 100 to disperse the nucleic acid-solid support complex in the eluent. The eluent may be directly injected to the filter column 100 manually, or may be supplied from the eluent storage unit 170 that is detachably connected to an opening of the filter column 100 which is disposed to correspond to the elution direction of nucleic acids, or an opening of the filter column 100 which is disposed to correspond to the direction opposite the elution direction of nucleic acids. The flow of eluent to the filter column 100 from the eluent storage unit 170 may be adjusted by the second adjustment unit 200 that is connected to the eluent storage unit 170. The dispersion of the nucleic acid-solid support complex in the eluent is performed by the dispersion unit 150. The dispersion unit 150 may be a pressurizing device, or a sonicator, that is detachably connected to a bottom opening of the filter column 100 which is disposed to correspond to the elution direction of nucleic acids, or a top opening of the filter column 100 which is disposed to correspond to the direction opposite the elution direction of the nucleic acids, to allow fluid flow therebetween. The nucleic acid-solid support complex is fully dispersed in the eluent in the filter column 100 by a pressurized gas generated from the pressurizing device, or by ultrasonic waves generated from the sonicator. During this process, nucleic acids are eluted to the eluent from the nucleic acid-solid support complex, that is, the nucleic acids are released from the nucleic-acid binding support into the eluent. Adjustment of the pressure from the pressurizing device, or adjustment of the ultrasonic waves from the sonicator, is performed by the dispersion adjustment unit 220. The pressure or ultrasonic waves adjusted by the dispersion adjustment unit 220 may occur in a repetitive pattern, for example a cycle that consists of a pulse and a rest period, and the adjustment may be automatically performed by the dispersion adjustment unit 220 under a program. The separation of the eluent from the nucleic acid-binding solid support may be performed using a well-known method in the art.

When the apparatus for isolating nucleic acids includes the sample storage unit 180 as illustrated in FIG. 2, the nucleic acid-solid support complex 130 may be formed by contacting the nucleic acid-binding solid support with the nucleic acid-containing sample in the sample storage unit 180. The nucleic acid-solid support complex 130 is supplied to the filter column 100 from the sample storage unit 180, and as a result, the filter column 100 is filled with the nucleic acid-solid support complex 130. The sample storage unit is detachably connected to an opening of the filter column 100 which is disposed to correspond to the elution direction of nucleic acids, or to an opening of the filter column 100 which is disposed to correspond to the direction opposite the elution direction of the nucleic acids. The sample flow to the filter column 100 from the sample storage unit 180 may be adjusted by the third adjustment unit 210 that is connected to the sample storing unit 180. The nucleic acid-solid support complex 130 is then washed and eluted using the methods described above. As a result, nucleic acids may be eluted to the eluent.

In the following example, nucleic acids are isolated using apparatuses for isolating nucleic acids, according to the above one or more embodiments, and the efficiencies of the apparatuses are tested.

EXAMPLE 1

Binding of nucleic acids in a nucleic acid-containing sample to a solid support in a filter column and elution of nucleic acids An AN25 filter (Millipore) having a pore size of 2.5 µm was installed in the bottom opening of a column (Qiagen) to make a filter column. Beads (30 µl of carboxyl-coated polystyrene beads having a diameter of 4 µm; (Bangs Lab)), dNTP and nucleic acid (PCR amplicons, 203 µg of DNA) were mixed in a microtube in the presence of a PEG solution (20% polyethylene, 2.5M NaCl), and a bead-nucleic acid complex was formed. The filter column was packed with the prepared bead-nucleic acid complex under reduced pressure (~−75 kPa) in a vacuum. 2 ml of 70% ethanol was then added to the filter column and DNA that was not bound to the beads, along with impurities, were removed under reduced pressure in a vacuum. The beads were dried for 15 minutes under reduced pressure in a vacuum again, and 80 µl of a nucleic acid eluent ($dH_2O$) was added thereto. Thereafter, a pressurized nitrogen gas generated from a pressurizing device that was connected to the bottom of the filter column via a rubber tube, was injected into the nucleic acid eluent containing the beads to which DNA was bound for a period of 15 minutes at a pressure of −20 kPa (Refer to FIG. 3). The beads to which DNA was bound were then fully dispersed in the nucleic acid eluent. The filter column was then put in a centrifugal separator and centrifuged for 30 seconds at a speed of 13,200 rpm to obtain a DNA eluent.

The concentration, total amount, and yield of DNA in the obtained DNA eluent are shown in Table 1 below.

TABLE 1

| Sample | Concentration (ng/µl) | Elution volumn (µl) | Total amount (µg) | Yield (%) | 260/280 | 260/230 |
|---|---|---|---|---|---|---|
| 1 | 2166.8 | 75 | 162.5 | 80.1% | 1.88 | 2.33 |
| 2 | 1995.6 | 76 | 151.7 | 74.7% | 1.86 | 2.31 |
| 3 | 2126.7 | 75 | 159.5 | 78.6% | 1.84 | 2.29 |
| 4 | 2180.6 | 75 | 163.5 | 80.6% | 1.88 | 2.18 |
| 5 | 2033.2 | 79 | 160.6 | 79.1% | 1.87 | 2.32 |

Average concentration: 2100.6 ng/µl, average total amount: 159.6 µg, average yield: 78.6%

As shown in Table 1, in the above experiment, 80 µl of the eluent was used and about 75 to about 79 µl of the DNA eluent was obtained. The average DNA concentration, the average total amount of DNA, and the average yield of DNA were 2100.6 ng/µl, 159.6 µg, and 78.6%, respectively. In addition, referring to Table 1, the ratio of absorbance at 260 nm to absorbance at 280 nm (DNA/protein) is 1.84:1 to 1.88:1, and a ratio of absorbance at 260 nm to absorbance at 230 nm (DNA/salt) is 2:1 or greater. From these results, the isolated DNA was confirmed to have a high degree of purity.

In a QIAquick PCR purification kit manufactured by Qiagen, the maximum amount and volume of nucleic acids that are purified are 10 µg and 800 µl, respectively (Qiagen spin handbook). Therefore, it was impossible to treat the sample at once using the kit.

EXAMPLE 2

Evaluation of Elution Efficiency of Polynucleotides by Adjusting Amount of Solid Support and Pressure A filter (cellulose acetate, Advantec) having a pore size of 3 µm was installed in the bottom opening of a column (prepared by an experimenter) to make a filter column. Beads (30 µl of carboxyl-coated polystyrene beads having a diameter of 4 µm (Bangs Lab)) and a polynucleotide fragment (about 1000 to 2000 bp, 102.6 ng/µl) were mixed in a microtube for 10 minutes in the presence of a PEG solution (20% polyethylene, 2.5M NaCl), and the filter column was packed with the prepared bead-nucleic acid complex under pressure (150 kPa) for 8 minutes. The level of purification and enrichment of the polynucleotide fragment were simultaneously evaluated by increasing the volume of the polynucleotide fragment. 1 ml of 75% ethanol was then added to the filter column under pressure to remove polynucleotides that were not bound to the beads and any impurities. The filter column was pressurized at 75 kPa for 2 minutes and at 112.5 kPa for 1 minute, the beads were dried under the initial pressurizing condition (150 kPa) for 30 seconds, and 50 µl of a nucleic acid eluent (dH$_2$O) was added thereto. Thereafter, a pressurized nitrogen gas generated from a pressurizing device that was connected to the bottom of the filter column via a rubber tube was injected into the nucleic acid eluent containing the beads to which the polynucleotide fragment was bound at pressures of 70 kPa, 60 kPa, and 50 kPa for a period of 5 minutes each. The pressurizing conditions used were a pulse of 2 seconds and a rest period of 8 seconds. Thereafter, the resultant product was pressurized at 150 kPa for 5 minutes to obtain a polynucleotide-containing eluent.

The concentration, total amount and yield of polynucleotides in the obtained polynucleotide eluent were quantified by an ultraviolet ray and picogreen dye, and the results are shown in Table 2 below.

TABLE 2

| Sample | Concentration of nucleic acids added (ng/µl) | Volume of nucleic acid solution added (µl) | Concentration of nucleic acids purified (ng/µl) | Total amount of nucleic acids purified (µg) | Yield (%) | Enrichment ratio of nucleic acids (times) | 260/280 |
|---|---|---|---|---|---|---|---|
| Added nucleic acids | 102.6 | | | | | | 1.62 |
| 1 | 102.6 | 100 | 157.1 | 7.85 | 82 | 1.53 | 1.89 |
| 2 | 102.6 | 500 | 902 | 45.1 | 88 | 8.79 | 1.85 |
| 3 | 102.6 | 1000 | 1730 | 86.5 | 84 | 16.9 | 1.90 |
| 4 | 102.6 | 2000 | 3795 | 189.8 | 92 | 37.0 | 1.88 |

As shown in Table 1, nucleic acids were effectively purified using 50 µl of the eluent. In addition, it was confirmed that even a low concentration of nucleic acids in a sample was enriched to a high concentration, and the yield of nucleic acids was 80% or greater. Moreover, as shown in Table 1, the ratio of absorbance at 260 nm to absorbance at 280 nm (DNA/protein) is 1.8 or greater, and from the results, it was confirmed that the isolated polynucleotides had a high purity. Meanwhile, an experiment was performed using the same method as in Example 3, except that the nucleic acid eluent containing the beads to which the polynucleotide fragment was bound was constantly pressurized at 50 kPa for 20 minutes without a pulse and a rest period. As a result of the experiment, the nucleic acid eluent was intermittently overflowed in the filter column, and thus the desired polynucleotide-containing eluent was not obtained.

As described above, according to the one or more exemplary embodiments, a method of isolating nucleic acids in a high concentration and an apparatus for isolating nucleic acids are provided. A high concentration of nucleic acids may be efficiently eluted and isolated from a nucleic acid-containing sample using only a small amount of an eluent.

The present invention should not be construed as being limited to the embodiments set forth herein. Rather, these embodiments are provided so that this disclosure will be thorough and complete and will fully convey the general inventive concept to those skilled in the art.

While the present invention has been particularly shown and described with reference to embodiments thereof, it will be understood by those of ordinary skill in the art that various changes in form and details may be made therein without departing from the spirit or scope of the present invention as defined by the following claims.

What is claimed is:

1. A method of isolating nucleic acids, the method comprising:

contacting a nucleic acid-containing sample with a nucleic acid-binding solid support to bind a nucleic acid to the nucleic acid-binding solid support, thereby forming a nucleic acid-solid support complex;

washing the nucleic acid-binding solid support to remove nucleic acid-containing sample that is not bound to the nucleic acid-binding solid support after the contacting;

adding an eluent to the nucleic acid-solid support complex;

dispersing the nucleic acid-solid support complex in the added eluent by injection of pressurized gas or adding ultrasonic waves to the eluent; and separating the eluent from the nucleic acid-binding solid support, wherein the dispersing is performed by adjusting the pressure of the pressurized gas or an intensity of the ultrasonic waves for a constant period of time, and wherein the adjusting of the pressure of the gas or the adjusting of the intensity of the ultrasonic waves is performed by sequentially performing a pulse and a rest thereby releasing the nucleic acid from the nucleic acid-solid support complex.

2. The method of claim 1, wherein the method comprises adjusting of the intensity of ultrasonic waves by repeatedly sequentially performing a pulse and a rest.

3. The method of claim 1, wherein the method comprises adjusting of the pressure of a gas by repeatedly sequentially performing a pulse and a rest.

4. The method of claim 1, wherein the nucleic acid-binding solid support is selected from the group consisting of a magnetic bead, a silica bead, a polystyrene bead, a glass bead, and a cellulose bead.

5. The method of claim 1, wherein an amount of the eluent added is about 10 µl to about 500 µl.

6. The method of claim 1, wherein the nucleic acid-binding solid support has a diameter of about 0.1 µm to about 50 µm.

* * * * *